United States Patent
Younge et al.

(10) Patent No.: US 8,290,571 B2
(45) Date of Patent: Oct. 16, 2012

(54) AUXILIARY CAVITY LOCALIZATION

(75) Inventors: Robert G. Younge, Portola Valley, CA (US); Bhaskar S. Ramamurthy, Los Altos, CA (US); Randall L. Schlesinger, San Mateo, CA (US); Neal A. Tanner, Mountain View, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 561 days.

(21) Appl. No.: 12/507,706

(22) Filed: Jul. 22, 2009

(65) Prior Publication Data

US 2010/0048998 A1 Feb. 25, 2010

Related U.S. Application Data

(60) Provisional application No. 61/137,628, filed on Aug. 1, 2008.

(51) Int. Cl.
*A61B 5/00* (2006.01)
(52) U.S. Cl. .......................... 600/424; 702/95
(58) Field of Classification Search .................. 600/424; 702/94–95; 356/614
See application file for complete search history.

(56) References Cited

U.S. PATENT DOCUMENTS

| | | | | |
|---|---|---|---|---|
| 5,391,199 A | * | 2/1995 | Ben-Haim | 607/122 |
| 5,983,126 A | * | 11/1999 | Wittkampf | 600/509 |
| 6,263,230 B1 | * | 7/2001 | Haynor et al. | 600/424 |
| 2004/0097803 A1 | * | 5/2004 | Panescu | 600/424 |
| 2005/0137478 A1 | | 6/2005 | Younge et al. | |
| 2005/0197530 A1 | | 9/2005 | Wallace | |
| 2005/0222554 A1 | | 10/2005 | Wallace | |
| 2006/0057560 A1 | | 3/2006 | Hlavka | |
| 2006/0084945 A1 | | 4/2006 | Moll | |
| 2006/0095022 A1 | | 5/2006 | Moll | |
| 2006/0100610 A1 | | 5/2006 | Wallace et al. | |
| 2006/0111692 A1 | | 5/2006 | Hlavka | |
| 2006/0200026 A1 | | 9/2006 | Wallace | |
| 2006/0253108 A1 | | 11/2006 | Yu et al. | |
| 2006/0276775 A1 | | 12/2006 | Rosenberg | |
| 2006/0293643 A1 | | 12/2006 | Wallace et al. | |
| 2007/0043338 A1 | | 2/2007 | Moll et al. | |
| 2007/0156019 A1 | * | 7/2007 | Larkin et al. | 600/104 |
| 2007/0156123 A1 | | 7/2007 | Moll | |
| 2007/0197896 A1 | | 8/2007 | Moll et al. | |
| 2007/0197939 A1 | | 8/2007 | Wallace et al. | |
| 2007/0233044 A1 | | 10/2007 | Wallace et al. | |
| 2007/0265503 A1 | | 11/2007 | Schlesinger | |
| 2008/0027464 A1 | | 1/2008 | Moll et al. | |
| 2008/0058836 A1 | | 3/2008 | Moll et al. | |
| 2008/0082109 A1 | | 4/2008 | Moll et al. | |
| 2008/0119727 A1 | | 5/2008 | Barbagli et al. | |
| 2008/0140087 A1 | | 6/2008 | Barbagli | |
| 2008/0167750 A1 | | 7/2008 | Stahler et al. | |
| 2008/0195081 A1 | | 8/2008 | Moll | |
| 2008/0218770 A1 | | 9/2008 | Moll et al. | |
| 2008/0243063 A1 | | 10/2008 | Camarillo | |
| 2008/0243064 A1 | | 10/2008 | Stahler et al. | |
| 2008/0245946 A1 | | 10/2008 | Yu | |
| 2008/0249536 A1 | | 10/2008 | Stahler et al. | |
| 2008/0262480 A1 | | 10/2008 | Stahler et al. | |

(Continued)

*Primary Examiner* — Jonathan Cwern

(57) ABSTRACT

A method and system for maintaining calibration of a distributed localization system are presented. After a baseline calibration of sensors distributed on a working instrument and reference instrument, if movement of the reference instrument is detected, shape sensing data from a Bragg shape sensing fiber also coupled to the reference instrument may be utilized to recalibrate the localization system. The reference instrument preferably is located intraoperatively in a relatively constrained anatomical environment, such as in the coronary sinus of the heart, to prevent significant movement.

15 Claims, 2 Drawing Sheets

U.S. PATENT DOCUMENTS

| | | |
|---|---|---|
| 2008/0262513 A1 | 10/2008 | Stahler et al. |
| 2008/0285909 A1 | 11/2008 | Younge et al. |
| 2008/0312521 A1 | 12/2008 | Solomon |
| 2008/0312713 A1 | 12/2008 | Wilfley et al. |
| 2009/0036900 A1 | 2/2009 | Moll |
| 2010/0030063 A1* | 2/2010 | Lee et al. .................. 600/424 |

* cited by examiner

AUXILIARY CAVITY LOCALIZATION

RELATED APPLICATION DATA

The present application claims the benefit under 35 U.S.C. §119 to U.S. Provisional Patent application Ser. No. 61/137,628, filed Aug. 1, 2008. The foregoing application is hereby incorporated by reference into the present application in its entirety.

FIELD OF INVENTION

The invention relates generally to remotely controlled medical devices and systems, such as telerobotic surgical systems or manually steerable catheters, and the employment thereof for conducting procedures in the heart, blood vessels, and other body lumens. More particularly, this invention relates to systems, apparatuses, and methods detecting the position of one or more instruments within one or more targeted tissue cavities during a minimally invasive diagnostic or therapeutic procedure.

BACKGROUND

It is generally desirable in minimally invasive medical procedures involving instruments such as catheters, probes, and the like to understand the spatial positioning of such instruments relative to nearby tissue structures, such as the walls of a cavity of a heart. In the cardiovascular market, for example, several systems are available for tracking position, or "localizing", instruments—including but not limited to the system sold under the tradename "EnSite™" by St. Jude Medical, Inc., and the system sold under the tradename "CartoXP™" by the Biosense Webster division of Johnson & Johnson, Inc. The EnSite system utilizes potential differences between reference patches and instruments to localize instruments while the CartoXP system utilizes magnetic fields and currents detected by small coils coupled to an instrument to localize such instrument. Fiber bragg (hereinafter "FBG") sensor technology and configurations have been disclosed, for example in U.S. Patent Applications 60/785,001, 60/788,176, 60/899,048, 60/900,584, 11/690,116, 60/925,449, 60/925,472, 60/964,773, 61/003,008, 12/012,795, 12/106,254, the entirety of which are incorporated herein by reference, which allow for localization and shape sensing of elongate instruments. Depending upon the particular FBG configuration, such technology may enable not only localization of particular points along an elongate instruments, as with the aforementioned localization technologies, but also localization of the spatial position of an entire section of the length of such instrument—or the entire length of the instrument, for that matter. It would be advantageous to combine certain aspects of FBG localization and shape sensing technologies with more conventional localization technologies, such as those available from Biosense or St. Jude Medical, to provide a hybrid localization system capable of addressing certain shortcomings of the systems as individually deployed. Several such configurations are described here.

SUMMARY OF THE INVENTION

Figure 1:
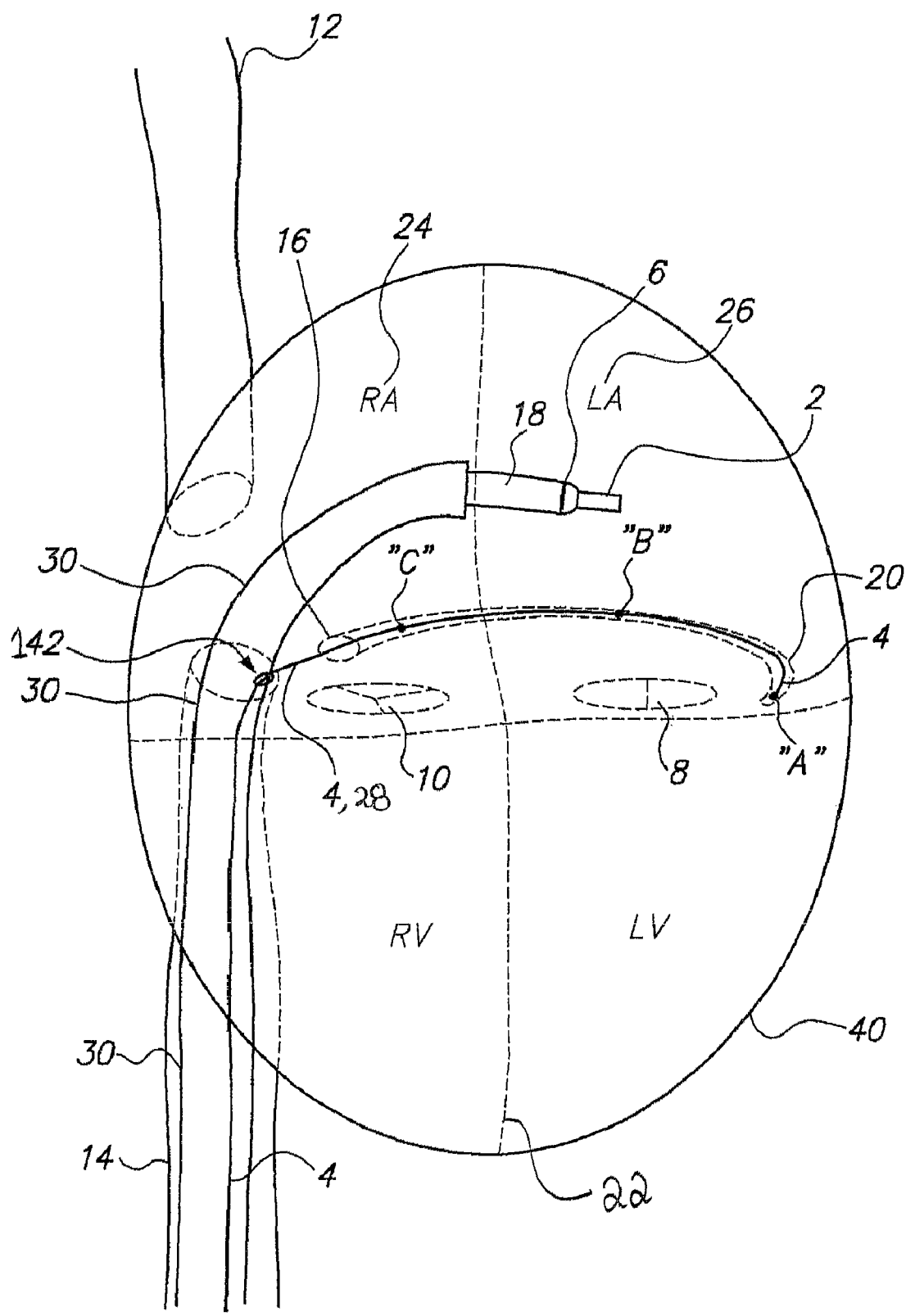
FIG. 1 illustrates a system level view of a referenced localized configuration in accordance with one embodiment of the present invention.

One embodiment is directed to a localized medical instrument system comprising an elongate medical instrument having a distal tip; a reference medical instrument having a distal tip and a distal portion proximal to the distal tip; a localization system comprising a localization controller and one or more discrete localization sensors, the localization controller configured to output spatial positional information regarding the one or more localization sensors; a fiber Bragg shape sensing system comprising a Bragg controller and one or more shape sensing Bragg fibers having one or more Bragg gratings distributed thereon, the Bragg controller configured to output shape data; and a system controller operatively coupled to the localization controller and Bragg controller; wherein one or more localization sensors are coupled to the elongate medical instrument and operatively coupled to the localization controller; wherein one or more localization sensors are coupled to different known longitudinal positions along the distal portion of the reference medical instrument and operatively coupled to the localization controller; wherein the one or more shape sensing Bragg fibers are coupled to the reference medical instrument and operatively coupled to the Bragg controller; and wherein subsequent to an initial calibration of the localization system using localization sensor spatial positions on the elongate medical instrument relative to those on reference medical instrument, and of the localization sensor spatial positions on the reference medical instrument relative to the Bragg controller shape data, the system controller is configured to operate the localization controller to determine the position of the elongate medical instrument utilizing the one or more localization sensors coupled to the elongate medical instrument and the reference medical instrument, and to automatically recalibrate the localization system based upon changes in position or shape of the reference medical instrument detected by the localization and shape sensing systems. The elongate medical instrument may be a catheter. The reference medical instrument may be a slender probe configured to be placed into an anatomic pathway. The slender probe may be configured to be placed into the coronary sinus of the heart. The localization system may be a potential difference based localization system. The localization sensors on the reference medical instrument may be reference sensors utilized to facilitate determining positional information of localization sensors coupled to the elongate medical instrument. At least one of the one or more localization sensors coupled to the elongate medical instrument may be physically integrated into the elongate medical instrument. At least one of the one or more localization sensors coupled to the reference medical instrument may be physically integrated into the reference medical instrument. The localization system may be an electromagnetic based localization system. The fiber Bragg shape sensing system comprises one or more Bragg fibers having continuous or substantially continuous gratings along portions thereof. The fiber Bragg shape sensing system may comprise one or more Bragg fibers having discrete gratings along portions thereof. The fiber Bragg shape sensing system may comprise an integrated multi-core fiber bundle. The fiber Bragg shape sensing system may comprise one or more single-core fibers. The one or more shape sensing Bragg fibers may be physically integrated into the reference medical instrument. Three or more localization sensors may be positioned at different known longitudinal positions with a substantially equal spacing between adjacent sensors.

Another embodiment is directed to a method for maintaining calibration of a medical device localization system, comprising establishing a baseline calibration between the positions of one or more localization sensors coupled to an elongate medical instrument and one or more localization sensors coupled to a nearby reference medical instrument at known longitudinal positions along the instrument; and detecting repositioning of the reference medical instrument utilizing a fiber Bragg shape sensing system comprising one or more shape sensing Bragg fibers coupled to the reference medical instrument. The method may further comprise notifying an operator of the elongate medical instrument that a recalibration is required. The method may further comprise stopping any automated motion associated with the elongate medical instrument. Detecting repositioning may comprise saving in a buffer a predetermined amount of data pertinent to the positioning of the reference medical instrument and comparing such buffer data to newly determined positioning data. The method may further comprise automatically recalibrating the positions of the one or more localization sensors coupled to an elongate medical instrument and the one or more localization sensors coupled to a nearby reference medical instrument based upon changes in position or shape of the reference medical instrument detected by the localization and shape sensing systems. The method may further comprise positioning the elongate medical instrument adjacent targeted tissue structures, and positioning the reference medical instrument nearby in a substantially more constrained position relative to nearby anatomy, to prevent substantial motion of the reference medical instrument. The elongate medical instrument may be placed within one of the chambers of the heart. The reference medical instrument may be placed within the coronary sinus of the heart. The method may further comprise retracting and repeating positioning the reference medical instrument nearby in the substantially more constrained position relative to nearby anatomy, to gather additional data regarding the shape of the anatomy.

DETAILED DESCRIPTION OF THE ILLUSTRATED EMBODIMENTS

Referring to FIG. 1, an exemplary tissue structure complex comprising the right atrium, left atrium, inferior vena cava, superior vena cava (12), tricuspid valve (10), mitral valve (8), and coronary sinus is depicted for illustration purposes. Such tissue structures may be navigated and/or investigated utilizing a robotic catheter system comprising, for example, an outer steerable sheath catheter (30) and a coaxially-associated inner sheath catheter (18), such as those described with similar element labels in patent application Ser. Nos. 10/923,660, 10/949,032, 11/073,363, 11/173,812, 11/176,954, 11/179,007, 11/176,598, 11/176,957, 11/185,432, 11/202,925, 11/331,576, 11/418,398, 11/481,433, 11/637,951, 11/640,099, 11/678,001, 11/678,016, 60/919,015, 11/690,116, 60/920,328, 60/925,449, 60/925,472, 60/926,060, 60/927,682, 11/804,585, 60/931,827, 60/934,639, 60/934,688, 60/961,189, 11/762,778, 11/762,779, 60/961,191, 11/829,076, 11/833,969, 60/962,704, 60/964,773, 60/964,195, 11/852,252, 11/906,746, 61/003,008, 11/972,581, 12/022,987, 12/024,883, 12/024,760, 12/024,641, 12/032,626, 12/032,634, 12/032,622, 12/032,639, and 12/012,795, each of which is incorporated by reference in its entirety into this disclosure. A working instrument (2), depicted through the working lumen of the guide instrument (18), may be configured to map the electrical activity of the inside of the heart, ablate related tissues, inject, grasp, etc, as described in the aforementioned incorporated applications. Other remotely steerable systems, including those that are manually steered with handles and the like rather than electromechanical instrument driving mechanisms, may also be utilized for the subject procedures, systems, and apparatuses.

The coronary sinus (hereinafter "CS") has a relatively unique anatomical geometry which substantially retains its form throughout the heart cycle. In other words, as one examines the shape of the CS, there are certain turns along its length that are substantially, but not entirely, retained as turns throughout the heart cycle. This presents a shape sensing opportunity. To maintain accurate localization of a working instrument configuration such as that depicted in FIG. 1, a reference instrument (4) comprising a FBG shape-sensing fiber having multiple sensors along its length may be placed in the CS, and the pattern of bending strain (detected via FBG shape sensing) along the length of such reference instrument (4) may be utilized to assist in the understanding of position detection of the associated working instrument configuration.

An illustrative embodiment is useful in describing further details regarding the foregoing improvement. Referring to FIG. 1, a conventional localization system is utilized to monitor the position of one or more sensors (6) coupled to the working instrument assembly (30, 18, 2)—in the depicted embodiment a single sensor (6) is coupled to the distal portion of the guide instrument (18); in other embodiments, more sensors may be coupled to the instrument assembly at other positions along the various instruments comprising the assembly. Each localization sensor preferably is operably coupled to a localization system (not shown) via an electronic coupling such as a thin conductive member or wire, which may comprise the body of one of the members (4). The localization sensors may be directly coupled to a surface of an associated instrument, or they may be physically integrated into the body of such instrument. Suitable localization systems, such as those available from the Biosense Webster division of Johnson and Johnson, Inc. under the tradename CartoXP®, Boston Scientific Corporation under the tradename RPM®, or St. Jude Medical, Inc. under the tradename EnSite®, are configured to output position and/or orientation information regarding each sensor, and may be operably coupled to an electromechanical instrument operation computing and/or controller system, such as those described in the aforementioned incorporated by reference applications, which may be operatively coupled to an electromechanical instrument driver configured to operate the instruments, also as described in the aforementioned incorporated by reference applications. Conventionally, a reference instrument may be placed in the vicinity of the working instrument assembly (30, 18, 2) having a series of localization sensors spaced apart longitudinally along the reference instrument at known lengths. The combination of these known spacing separations, and the data (potential difference or current data, for example) gathered from each reference instrument sensor, and the data (potential difference or current data, for example) gathered from the working instrument assembly sensor (6) may be utilized to determine the position of the working instrument assembly sensor (6) in space, in near-real-time. With such a configuration, if the reference instrument suddenly moves relative to the working instrument and/or anatomy, the system's understanding of the relationships between the various instruments generally is thrown off and the system needs to be recalibrated before precision localization of the working instrument assembly can continue. One solution to this challenge is to place the reference instrument into a relatively confined position, such as threaded into the CS. However, in the event that the reference instrument moves during a procedure (for example, as a result of heart movement, breathing, loads applied to associated structures, etc) relative to the confining structures (such as the CS), the system's understanding of the relationships between the reference instrument sensors and the working instrument assembly sensors are again thrown off. This problem may be remedied by associating fiber bragg sensing technology with the reference instrument—so that changes in the position of the reference instrument may be characterized in near-real-time, and so that the coordination of the reference catheter sensors and the working catheter assembly sensors may be continued. Referring again to FIG. 1, such an embodiment is depicted.

As shown in FIG. 1, a working instrument assembly (30, 18, 2) is positioned through the inferior vena cava (14), across the right atrium (24) of the heart (40). The guide (18) and working (2) instruments are placed across the atrial septum (22) into the left atrium (26), where it may be desirable to accomplish an interventional or diagnostic procedure. In the depicted embodiment, a single localization sensor (6) is coupled to the working instrument assembly at a location upon the distal end of the guide instrument (18); in other variations, one or more sensors may be placed at various locations along the assembly and instruments comprising the assembly. Also shown in FIG. 1, a reference instrument (4) is depicted positioned through the inferior vena cava, through the os (16) of the coronary sinus (20), and around the curved pathway defined by the coronary sinus (20). The reference instrument has three reference localization sensors (labeled A, B, and C in FIG. 1) spaced apart longitudinally at known distances, and preferably comprises a flexible probe, guidewire, or catheter coupled to a fiber bragg sensing fiber (28) in a manner such as those disclosed in the aforementioned incorporated FBG-related applications. In another embodiment, one or more localization sensors may be present, as opposed to three or more. The FBG fiber may comprise a series of discrete bragg gratings, or may be configured with a set of continuous or substantially continuous gratings, to provide high-resolution bending sensing along the length of the fiber positioned through the coronary sinus; the fiber may be a simple single core fiber, which is capable of sensing bending along the length of the fiber, or may comprise a multi-core fiber configuration with additional shape sensing capabilities, as described in the aforementioned incorporated FBG-related applications. Further, the fibers may be loosely coupled to the shape of the associated instrument, or may be physically integrated to the body of the associated instrument. With the FBG fiber (28) coupled to the reference instrument (4), and both positioned through the CS (20), turns in the anatomical geometry of the CS (20) are seen as increases in strain amplitude at the FBG analyzing system (not shown—available from suppliers such as Luna Innovations, Inc., Micron Optics, Inc., etc—described in the aforementioned FBG-related incorporated applications). Given both conventional localizing sensors and the bragg grating sensors along the length of the reference instrument (4), one is able to map bending strain (via the FBG system) versus localized position (via the conventional localization system) and have an effective "fingerprint" of the reference instrument relative to the coronary sinus (20) anatomy. Should the reference instrument (4) suddenly move relative to the coronary sinus (20) anatomy, the system preferably is configured to not only 1) detect such movement by seeing a shift in the positioning of the bends in the FBG fiber relative to the reference localization sensor positions; but also 2) automatically recalibrate the system for the movement due to the data acquired from the FBG fiber and reference localization sensors (i.e., the system understands that the reference instrument has shifted relative to the CS, and can calculate by how much based upon the bending location movement longitudinally along the FBG fiber and the localization data from the reference localization sensors (labeled A, B, and C in FIG. 1). A transformation matrix or similar controls tracking structure may be utilized to maintain the up-to-date relationship between the reference instrument and the working instrument.

In one embodiment, the system may be configured to stop (navigation or instruments, feedback of localization data, or both) or signal the operator upon determining that the reference catheter has moved relative to the CS. In one embodiment, the system may be configured to constantly buffer a relevant amount of reference instrument sensor position data, and detect a delta larger than a certain predetermined threshold amount to make a determination that the reference catheter has "moved" relative to the CS; such a threshold may be intraoperatively programmable to accommodate different localization system accuracies. As described above, once a move has been detected, the system may be configured to characterize the move, account for it in a transformation matrix, and continue with the operation with the relationships of the reference instrument and working instruments continually understood.

In another variation, in the event that it is determined that something in the localization system has moved, and it can be determined using the above techniques that the reference catheter has not moved relative to the anatomy, then it may be determined that another component of the reference system has moved, such as a potential difference contact patch in the EnSite localization system—and this problem may be addressed without a complete restart of such system.

Several techniques may be utilized for mapping the strain and localization of the reference sensor within the coronary sinus. In one embodiment the FBG-reference instrument complex may be inserted into the CS, then pulled out again to produce redundant data regarding strain (from bending) and localization mapping; such insertion and/or retraction may be automated by utilizing, in a robotic variation as depicted in FIG. 1 (suitable robotic catheter systems being described in the aforementioned incorporated applications), robotic navigation features such as "autoretract" or simple electromechanically actuated and/or controlled insertion and/or retraction. In another variation, such insertion/retraction may be repeated to produce a more refined knowledge of the strain/localization patterns associated with the CS anatomy longitudinally through the heart.

In one embodiment (not shown), the reference instrument may be delivered to the diagnostic or interventional theater using one or more components of the working instrument assembly, rather than independent delivery as shown in FIG. 1; for example, a reference instrument such as that depicted in FIG. 1 may be carried to the right atrium (24) by the sheath instrument (30), where it may exit the sheath instrument (30) through an aperture or the like and enter the right atrium and coronary sinus (20) as an independent instrument branching away from the sheath instrument (30). If carried to the theater by a relatively large and relatively stiff structure such as the depicted sheath instrument (30), the proximal portion of the reference instrument (4) positioned within the sheath (30) is likely to have relatively little active bending activity until the reference instrument (4) exits the sheath (30) and the distal tip branches away from the sheath (30). This branching away point (142) is likely to be seen through FBG fiber bending monitoring as an increase in strain amplitude activity—and thus a reference point may be tracked for such point to provide additional data to the localization systems, such as the ability to reject common mode errors in the monitoring of positions of the instruments (such as heart movement or breathing artifact). Indeed, in another embodiment not having any conventional localization sensors, a Y-shaped configuration having one FBG fiber along a working instrument assembly and another fiber branching away from such assembly and into another cavity such as the CS would enable common mode rejection benefits, and in an embodiment wherein such FBG fibers are multicore FBG fibers, such as tricore FBG fibers, the branching-off point could be utilized to monitor shape and location of the two instrument assemblies without additional localization sensors.

In another embodiment, a hybrid configuration may be utilized wherein a simple localization sensor, such as that (6) depicted in FIG. 1, may be placed upon a diagnostic or therapeutic instrument, and a FBG fiber (not shown—may be single or multiple fiber configuration) may be coupled to the body of the same instrument assembly proximal and/or distal of this localization sensor (6). Depending upon the localization system utilized, this would provide 5 or 6 degree of freedom localization of the sensor (6) location, and shape sensing of the body of the same instrument assembly. Further, impendance or complex impedance monitoring or other contact sensing techniques may be added to the instrument assembly functionality to provide contact mapping capability for mapping nearby tissue structures and cavities defined by them.

Figure 2:
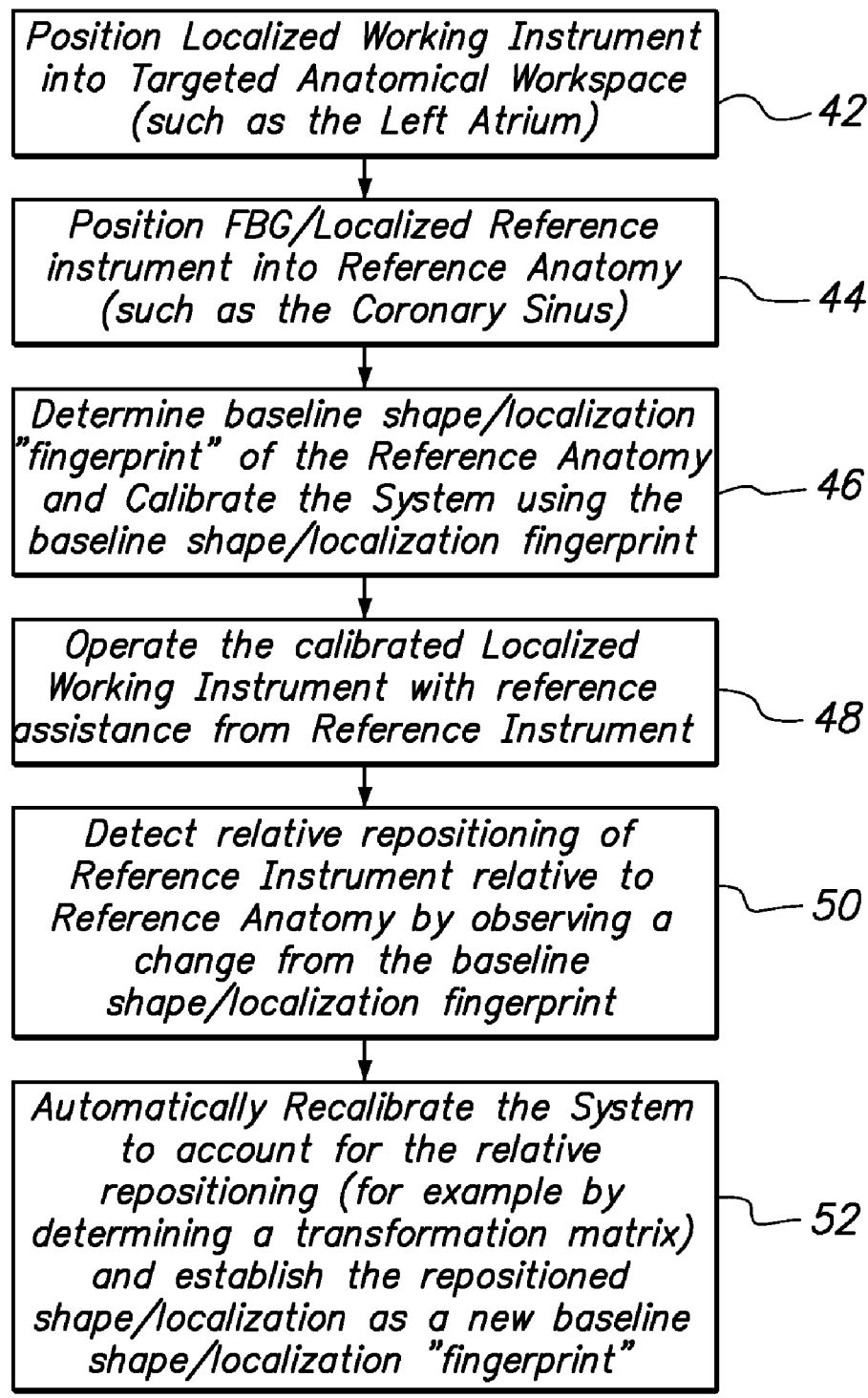
FIG. 2 illustrates a diagrammatic view of a referenced localized configuration in accordance with one embodiment of the present invention.

Referring to FIG. 2, a diagrammatic illustration of one embodiment of the subject calibration technology is depicted. A localized working instrument, such as a cardiac catheter, is placed in a targeted position relative to pertinent anatomy (42). A reference instrument which is both localized with localization sensors, and coupled to a Bragg shape sensing fiber, is placed in a reference anatomical position, generally selected such that the reference instrument will not accidentally become repositioned (44). A baseline "fingerprint" accounting for the relationship between the localization sensor data from the reference instrument and the localization sensor data from the working instrument, and also for the relationship between the localization sensor data (from the reference instrument localization sensors positioned at known longitudinal positions along the reference instrument) and the shape sensing data pertinent to the reference instrument (46). With everything calibrated, the working instrument may be operated and localized with reference to the reference localization sensors on the reference instrument (48). If there is repositioning of the reference instrument, this may be detected utilizing the shape and localization data pertinent to the reference instrument (50), and the system, comprising, for example, a system controller operatively coupled to both a localization controller (such as the aforementioned EnSite® device) and a shape sensing controller (such as the aforementioned systems available from Luna Innovations, Inc.) may use the data from both coupled controllers to automatically recalibrate, thereby taking into account the relative reposition, such as by determining a new or updated transformation matrix to apply when interpreting the data from both controllers (52).

These techniques may be utilized in other organs and cavities—the aforementioned examples wherein the coronary sinus is used as an auxiliary cavity adjacent the right or left atrium are for illustration purposes; the techniques may be broadly applied to assist in the accurate localization of instruments in cavities throughout the body, large and small, wherein an adjacent structure having a substantially predictable geometry which may be bending-mapped and monitored with a reference instrument is available.

While we have shown and described several embodiments in accordance with our invention, it should be understood that disclosed embodiments are susceptible to changes and modifications without departing from the scope of the invention. Therefore, we do not intend to be bound by the details shown and described herein but intend to cover all such changes and modifications that fall within the ambit of this written description.

The invention claimed is:

1. A localized medical instrument system, comprising:
   a. an elongate medical instrument having a distal tip;
   b. a reference medical instrument having a distal tip and a distal portion proximal to the distal tip;
   c. a localization system comprising a localization controller and one or more discrete localization sensors, the localization controller configured to output spatial positional information regarding the one or more localization sensors;
   d. a fiber Bragg shape sensing system comprising a Bragg controller and one or more shape sensing Bragg fibers having one or more Bragg gratings distributed thereon, the Bragg controller configured to output shape data; and
   e. a system controller operatively coupled to the localization controller and Bragg controller;
   wherein one or more localization sensors are coupled to the elongate medical instrument and operatively coupled to the localization controller;
   wherein one or more localization sensors are coupled to different known longitudinal positions along the distal portion of the reference medical instrument and operatively coupled to the localization controller;
   wherein the one or more shape sensing Bragg fibers are coupled to the reference medical instrument and operatively coupled to the Bragg controller; and
   wherein subsequent to an initial calibration of the localization system using localization sensor spatial positions on the elongate medical instrument relative to those on reference medical instrument, and of the localization sensor spatial positions on the reference medical instrument relative to the Bragg controller shape data, the system controller is configured to operate the localization controller to determine the position of the elongate medical instrument utilizing the one or more localization sensors coupled to the elongate medical instrument and the reference medical instrument, and to automatically recalibrate the localization system based upon changes in position or shape of the reference medical instrument detected by the localization and shape sensing systems.

2. The system of claim 1, wherein the elongate medical instrument is a catheter.

3. The system of claim 1, wherein the reference medical instrument is a slender probe configured to be placed into an anatomic pathway.

4. The system of claim 3, wherein the slender probe is configured to be placed into the coronary sinus of the heart.

5. The system of claim 1, wherein the localization system is a potential difference based localization system.

6. The system of claim 5, wherein the localization sensors on the reference medical instrument are reference sensors utilized to facilitate determining positional information of localization sensors coupled to the elongate medical instrument.

7. The system of claim 6, wherein at least one of the one or more localization sensors coupled to the elongate medical instrument are physically integrated into the elongate medical instrument.

8. The system of claim 6, wherein at least one of the one or more localization sensors coupled to the reference medical instrument are physically integrated into the reference medical instrument.

9. The system of claim 1, wherein the localization system is an electromagnetic based localization system.

10. The system of claim 1, wherein the fiber Bragg shape sensing system comprises one or more Bragg fibers having continuous or substantially continuous gratings along portions thereof.

11. The system of claim 1, wherein the fiber Bragg shape sensing system comprises one or more Bragg fibers having discrete gratings along portions thereof.

12. The system of claim 1, wherein the fiber Bragg shape sensing system comprises an integrated multi-core fiber bundle.

13. The system of claim 1, wherein the fiber Bragg shape sensing system comprises one or more single-core. fibers.

14. The system of claim 1, wherein the one or more shape sensing Bragg fibers are physically integrated into the reference medical instrument.

15. The system of claim 1, wherein three or more localization sensors are positioned at different known longitudinal positions with a substantially equal spacing between adjacent sensors.

* * * * *